United States Patent
Fang

(12)
(10) Patent No.: US 6,217,745 B1
(45) Date of Patent: Apr. 17, 2001

(54) METHOD FOR MONITORING AGENTS IN HYDROCARBON FLUIDS

(75) Inventor: Jiafu Fang, Spring, TX (US)

(73) Assignee: Pennzoil-Quaker State, Houston, TX (US)

( * ) Notice: Subject to any disclaimer, the term of this patent is extended or adjusted under 35 U.S.C. 154(b) by 0 days.

(21) Appl. No.: 09/379,628

(22) Filed: Aug. 24, 1999

(51) Int. Cl.$^7$ .................................................. G01N 27/26
(52) U.S. Cl. ........................ 205/775; 204/400; 204/409; 205/793.5; 205/787
(58) Field of Search .................................. 204/400, 409, 204/416; 205/775, 787, 793.5; 422/82, 82.03

(56) References Cited

U.S. PATENT DOCUMENTS

| | | | |
|---|---|---|---|
| 4,317,705 | 3/1982 | Hamada et al. | 205/780 |
| 4,333,810 | 6/1982 | Wolcott et al. | 204/418 |
| 4,744,870 | 5/1988 | Kauffman | 205/775 |
| 4,764,258 | 8/1988 | Kauffman | 205/786 |
| 5,071,527 | 12/1991 | Kauffman | 205/786 |
| 5,239,258 | 8/1993 | Kauffman | 205/786 |
| 5,518,590 | 5/1996 | Fang | 205/780.5 |

FOREIGN PATENT DOCUMENTS 1 206 079    6/1986   (CA) .

OTHER PUBLICATIONS

"Alcohol Fuels to Toxicology", Kirk–Othmer Encyclopedia of Chemical Technology, Supplement vol., Third Edition, John Wiley & Sons, 1984, pp. 46–47.

*Primary Examiner*—T. Tung
*Assistant Examiner*—Alex Noguerola
(74) *Attorney, Agent, or Firm*—Mcdermott, Will & Emery

(57) ABSTRACT

A method and apparatus uses a flow injection technique for rapidly and accurately determining the level of one or more additives such as antioxidants and/or antiwear agents in a hydrocarbon fluid such as an engine oil. The hydrocarbon fluid is injected into a mobile phase using a microemulsion or organic solvent as the mobile phase and pumped through an electrochemical detection sensor. The electrochemical detention sensor accurately and quickly provides a sharp signal identifying the electroactive species in the hydrocarbon fluid.

20 Claims, 2 Drawing Sheets

METHOD FOR MONITORING AGENTS IN HYDROCARBON FLUIDS

TECHNICAL FIELD

The present invention is directed to a method and apparatus for monitoring or determining the presence or absence of agents in hydrocarbon fluids and, in particular, to a method and apparatus which is particularly adapted to detect antioxidant and antiwear agents and their oxidation products in a lubricant such as an engine oil.

BACKGROUND ART

Hydrocarbon fluids such as engine oils, lubricants or the like are subject to conditions which cause the fluids to degrade over time. For example, oils in engines are subjected to pressures, frequent movement and heat which cause stresses to degrade the oil. Transmission fluids and other oils used in hydraulic systems are also susceptible to degradation over time. Cooking oils are another example of hydrocarbon fluids that may degrade over time.

Because of this degradation, antioxidants or antiwear agents are frequently added to hydrocarbon fluids such as oils, lubricants and the like to maintain their lubricating properties over time. For example, in using antioxidants, as long as the antioxidant remains intact, oxidation degradation of the hydrocarbon fluid is minimized so that it does not lose its desired properties.

Since using a hydrocarbon fluid beyond its useful life is undesirable, the prior art has developed various techniques and ways to monitor additives, agents or other components in hydrocarbon fluids to help determine whether the fluids still have any useful life.

In the prior art, different methods have been proposed to determine the remaining useful life of oils or the like. These methods vary in accuracy, easiness, efficiency, and economics.

In the prior art, a sensitive and simple electrochemical sensor is proposed to monitor the deterioration of a motor oil by determining the antioxidant and antiwear agent level remaining in the oil. In U.S. Pat. No. 5,518,590 to Fang, the present inventor, the electrochemical sensor is a device comprising a conductive liquid or gel-like electrolyte interphase separating the oil phase and the electrode surfaces, and is used on-line or off-line requiring no chemical or physical pretreatment of the oil.

In the prior art, cyclic voltammetry (CV) has been proposed to detect antioxidant and antiwear agents and their oxidation products in a lubricant, either on-line or off-line. U.S. Pat. Nos. 4,744,870, 4,764,258, 5,071,527 and 5,239,258, all to Kauffman, deal with this subject matter. U.S. Pat. No. 4,764,258 discloses an off-line method for evaluating a hydrocarbon fluid containing at least one additive species. An oil sample is mixed with a solvent and a solid subject to produce an analysis sample. The substrate settles from the analysis sample and then the analysis sample is placed into an electrolytic cell and subjected to voltammetric analysis. The additive may be a substituted phenol antioxidant or an oxidation product thereof. Alternatively, the additive species may be a metal-dithiodiphosphate multi-function additive or an oxidation product thereof.

In U.S. Pat. No. 5,071,527, the method of analysis includes applying an electrical potential to an electrode to produce an electrical current through the sample of oil, lubricant or fluid. The current can be produced with an extracted sample off-line or on-line with a continuously changing sample or with a sample in an on-line reservoir.

U.S. Pat. No. 4,744,870 discloses a method for measuring the remaining useful life of an ester-based lubricant containing at least one antioxidant species. A lubricant sample is mixed with a solvent, an organic base and an electrolyte to produce an analysis sample. The analysis sample is placed into an electrolytic cell and subjected to a cyclic voltammetric analysis. The current during this cyclicvoltammetric analysis is measured and recorded. Remaining useful life of the lubricant is then determined from the average maximum reduction current wave height produced.

The Kauffman patents cited above are incorporated by reference in their entirety, particularly for the purpose of identifying the types of hydrocarbon fluids and additives contemplated for use in the instant invention.

The methods using cyclic voltammetry to detect antioxidants and antiwear agents are not without their drawbacks. One skilled in the art recognizes that off-line CV wherein a solvent and an electrolyte are required works to a certain degree in determining the unreacted antioxidants such as alkylated phenols and aromatic amines. Since antioxidant and antiwear agents commonly used in the typical lubricant formulation are complicated mixtures, their signal response in CV is not well define, sensitive, or sharp and, therefore, often cannot be reproduced and accurately measured.

CV also does not work well in determining oxidation products in a lubricant due to the electrochemical inactivity of these products under conventional conditions for a CV test. On-line CV wherein electrodes are directly in contact with a lubricant, i.e., no solvent or electrolyte, does not work well since the oily components of the lubricants immediately cover the electrode surface, thereby rendering it non-functional.

In view of the drawbacks in the prior art techniques for determining the presence of additives, agents or the like in hydrocarbon fluids, particularly engine oils, a need has developed to provide an improved method and apparatus for these types of determinations.

In response to this need, the present invention provides both a method and apparatus for off-line applications which utilizes a flow injection method which can both rapidly and accurately determine or monitor the overall level of agents or additives such as antioxidants and antiwear agents in hydrocarbon fluids, particularly engine oils. While flow injection analysis is known when using converging streams of a sample and a reagent which mix and undergo chemical and physical change followed by monitoring by means of a flow-through detector, the prior art does not teach or suggest the inventive method or apparatus as described above.

DISCLOSURE OF THE INVENTION

Accordingly, it is a first object of the invention to provide a method and apparatus which permits rapid and accurate determination or monitoring of additives or the absence thereof in hydrocarbon fluids.

A further object of the present invention is a very sensitive, fast and highly reducible technique in determining antioxidant and antiwear agents in lubricants.

A still further object of the invention is a method and apparatus which avoids further treatment of samples when subjecting them to a determination or monitoring for the presence or absence of antioxidants, antiwear agents or the like.

Other objects and advantages of the present invention will become apparent as a description thereof proceeds.

In satisfaction of the foregoing objects and advantages, the present invention provides an apparatus for monitoring agents in hydrocarbon fluids comprising a source of the hydrocarbon fluid, a low pressure and low pulsation pump and a reservoir for storing a carrier capable of dissolving or emulsifying the hydrocarbon fluid. The reservoir is in communication with the pump so the pump pumps the carrier (the mobile phase) through an injector unit where the hydrocarbon fluid sample to be analyzed is injected and mixes with the carrier to form a mixed flow stream. The mixed flow stream is then introduced into an electrochemical detector. The electrochemical detector then responds to the electroactive species in the hydrocarbon fluid and provides a signal thereof indicative of the particular electroactive species present in the hydrocarbon fluid.

The inventive method is particularly adapted to detect typical antioxidants such hindered phenols and antiwear agents such as ZDDPs in oils. The carrier is preferably an microemulsion or organic solvent which dissolves a hydrocarbon oil without the need for any further treatment.

Once the mobile phase passes through the electrochemical sensor, it is discarded. The time in which the hydrocarbon fluid sample is subjected to the electrochemical detection can also be controlled by adjusting the flow rate of the mobile phase.

BRIEF DESCRIPTION OF DRAWINGS

Reference is now made to the drawings of the invention wherein.

BEST MODE FOR CARRYING OUT THE INVENTION

The inventive method and apparatus solves the problems associated with prior art CV methods for detecting additives and/or agents such as antioxidants and antiwear agents in hydrocarbon fluids such as engine oils, other lubricants or the like.

First, since the solvent of the invention dissolves the lubricant to be tested, no further treatment of the test sample is required prior to sensing for electroactive species in the hydrocarbon fluid.

Second, the inventive method and apparatus is fast, very sensitive and highly reproducible. A well-defined sharp signal response is given when sensing for the particular electroactive species, such a sharp signal not found in prior art methods using CV.

Figure 1:
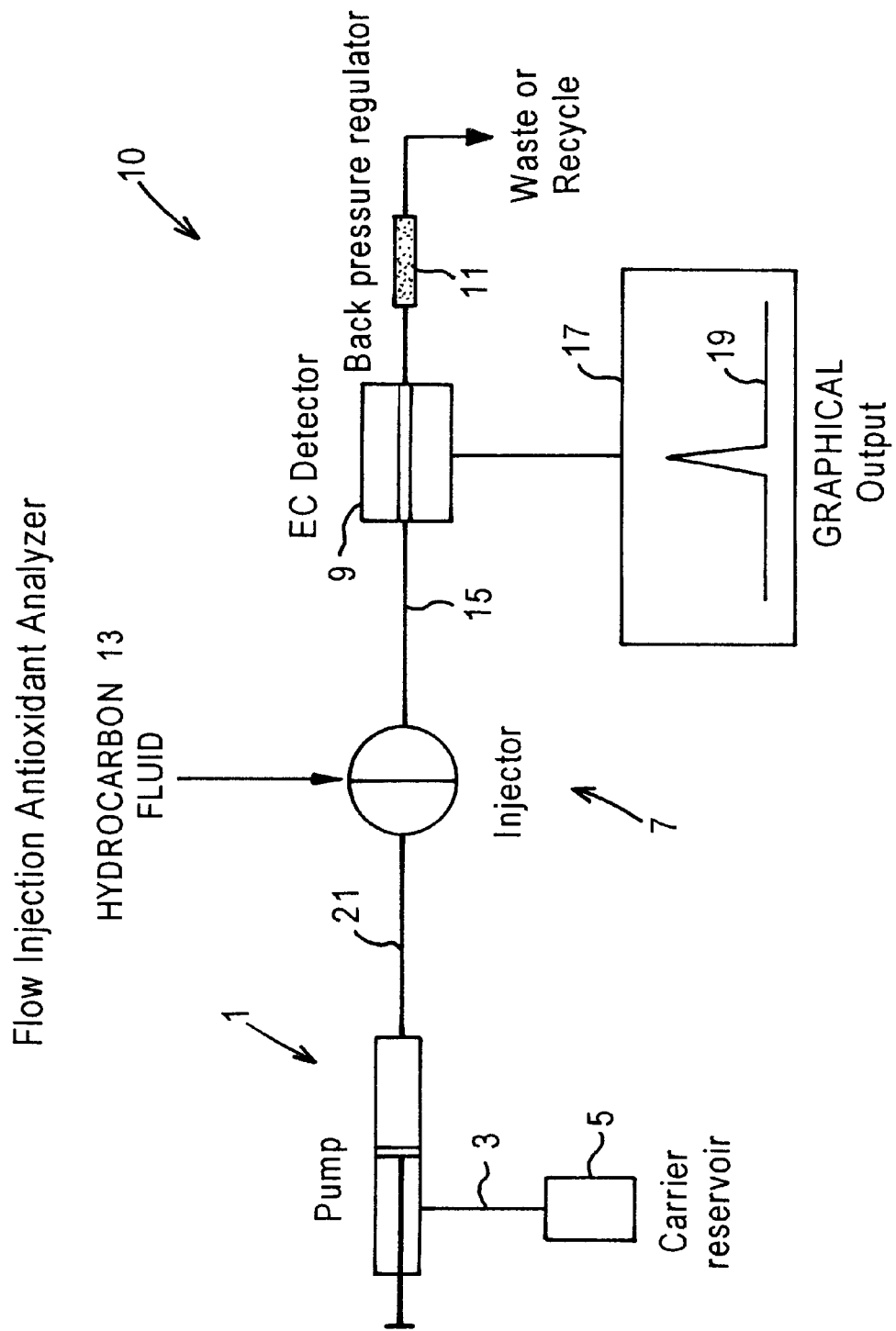
FIG. 1 is a schematic of the inventive apparatus.

FIG. 1 shows an exemplary apparatus designated by the reference numeral 10 for practicing the inventive method. A pump 1 is depicted which is in communication via line 3 with a reservoir 5 which holds the carrier for the hydrocarbon fluid to be treated. Although a reservoir 5 is shown, the carrier could be supplied in a continuous and metered fashion to the pump if so desired.

The pump is preferably a low pressure and low pulsation type, more preferably a pulseless type such as a syringe pump, whose flow rate is preferably adjustable.

The apparatus 10 also includes an injector 7, an electrochemical detector 9 and an optional back pressure regulator 11.

The reference numeral 13 is the hydrocarbon fluid to be analyzed, which can be directly delivered to the injector 7 and meet with the carrier phase there or be dissolved in the carrier solution before meeting with the carrier phase at the injector 7. The hydrocarbon fluid sample is then carried away by the carrier phase to the electrochemical detector 9 which responds to electroactive species in the sample such as antioxidants, antiwear agents and the like. The electrochemical detector provides a sharp signal response which is depicted in the form of the graphical output 17. The peak in the graph 19 represents the presence of the electroactive species and its height is proportional to the concentration of the electroactive species in the hydrocarbon fluid sample.

The back pressure regulator 11 is optional and is to reduce or eliminate gassing, if any, within the electrochemical detector once the test is over, the mobile phase 15 is either recycled or discarded.

In the method aspect of the invention, the hydrocarbon fluid 13 is combined with the carrier to form the mobile phase, either as a solution or an emulsification. The hydrocarbon fluid can be any type which is responsive to the electrochemical detector sensing, particularly oils or lubricants with antioxidants and antiwear agents such as those disclosed in the Kauffman patents referenced above.

The carrier can be an organic solvent or mixture of solvents such as acetonitrile and toluene with an electrolyte dissolved in it. Alternatively, the carrier can be a microemulsion consisting of ionic surfactants or combination of ionic and non-ionic surfactants. Use of ionic surfactants increases the conductivity of the carrier, hence avoiding the need for an additional electrolyte. Furthermore, Using these carriers permits dissolution or micro-emulsification of the test hydrocarbon fluid without the need for a further treatment prior to sensing by the electrochemical detector.

The test sample, is usually a functional hydrocarbon fluid such as engine oil, whose major constituent may be either a non-synthetic base oil or a synthetic one. Modern engine oil always contains additives such as antioxidants and antiwear agents, among others. Common antioxidants are substituted phenols and aromatic amines. Agents with multi-function properties are also commonly used, such as ZDDPs, that is, zinc dialkyldithiophosphates, which function both as antioxidant and antiwear agent. Antioxidant and antiwear agents aforementioned are usually electroactive and can be detected with an electrochemical detector. However, their oxidation products resulting from thermal degradation and mechanical stress inside the engine typically are not electroactive under conditions normally applied to the electrochemical detector and therefore cannot be detected.

Once the test sample is introduced into the mobile phase at the injector, it forms a sample zone in the stream and is carried away to the electrochemical detector for sensing of the electroactive species therein. The residence time of the sample zone in the electrochemical detector can be controlled and varied depending on factors such as the properties of the carrier, the test hydrocarbon fluid and the agents or additives to be tested for. One of the advantages of the invention is that the sensing of an antioxidant or antiwear agent can be done extremely rapidly, less than five minutes and, even less than three minutes for a typical motor oil sample.

In the present invention, during the electrochemical detector sensing step, the electroactive species in the hydrocarbon fluid such as a motor oil sends a very sensitive and sharp signal which is noted in terms of a detector response over time. This response indicates the level of the additive in the hydrocarbon fluid. Thus, one can subject a hydrocarbon fluid to the inventive method and determine whether the sought after additive or agent is still present. If no response or response below a certain level is received from the electrochemical detector, the hydrocarbon fluid being detected is no longer useful. For example, if a motor oil is checked for the presence of an antioxidant and no or little response is obtained when practicing the inventive method, the motor oil is said to be no longer useful and should be replaced in its given application.

Figure 2:
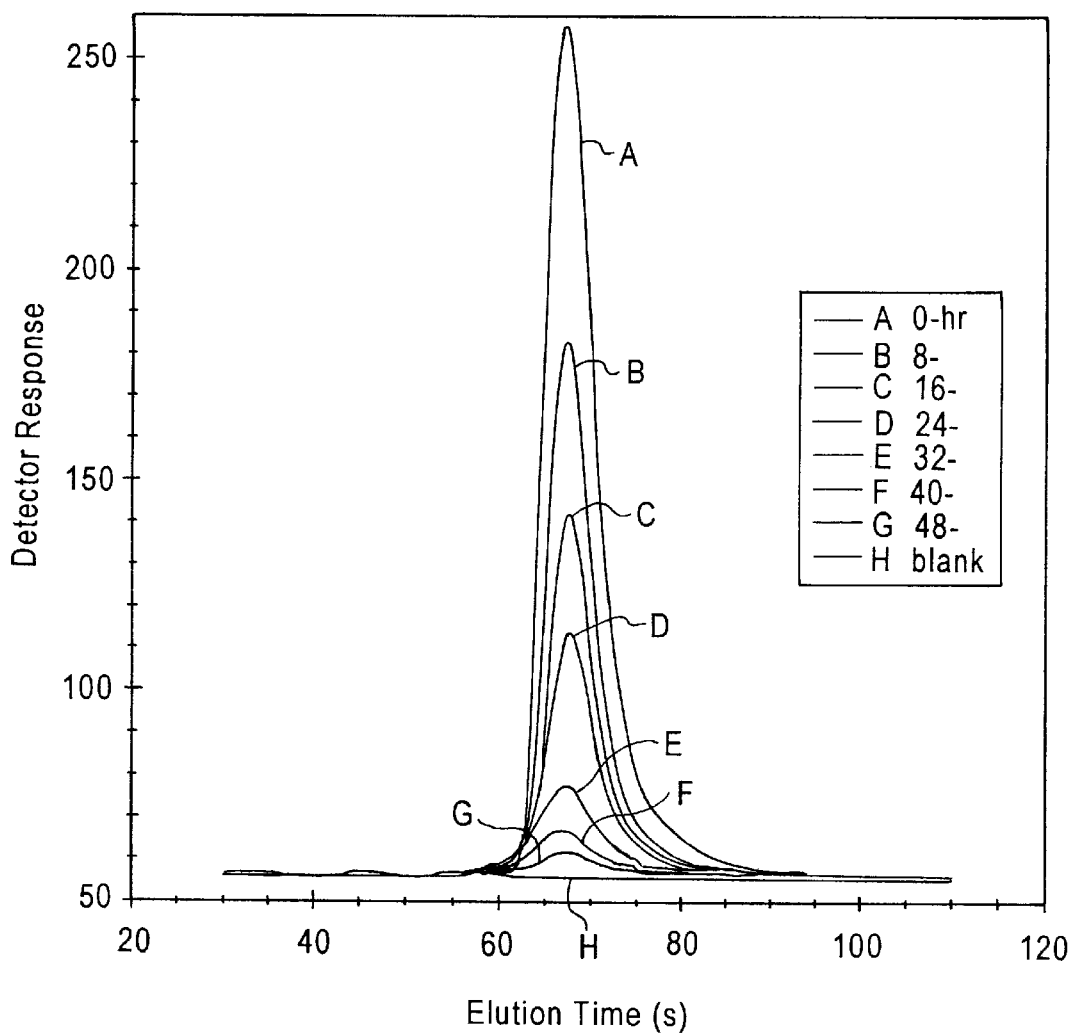
FIG. 2 is a graph showing a sharp signal response when testing a IIIE engine test sample for antioxidant/antiwear agent determination.

In demonstrating the utility of the invention, a IIIE engine test sample was used as a typical hydrocarbon fluid to determine the presence or absence of an antioxidant therein. Referring to FIG. 2, the detected response, which corresponds to the remaining level of antioxidant and antiwear agents in the oil, versus elution time, i.e., the sensing time is depicted for the IIIE engine test periods of 0–48 hours. A blank sample is also illustrated as a control. From FIG. 2, it is clear that the presence of an antioxidant in the IIIE engine test sample was detected using the inventive method and apparatus. The detected response for the antioxidant decreased over engine test time. This example clearly demonstrates that the method of monitoring agents for additives in hydrocarbon fluids by utilizing the inventive mobile phase or carrier consisting of a microemulsion or special solvent mixture as described above provides fast, sensitive and accurate measurements of these types of additives or agents. In conducting the test work disclosed in FIG. 2, the following details the testing parameters:

Referring again to FIG. 1, the signal from the electrochemical detector 9 is represented in graphical output. However, any known means of translating the signal from the detector 9 to a visual or other type of indications can be utilized for indicating the presence or absence of the additive or agent being detected.

If so desired, a plurality of electrochemical detectors could be used, either in parallel or in series relationship to monitor or determine the presence of multiple additives in the test hydrocarbon fluid 13. The pump capacity of the pump 1 could then be altered to account for the increased flow and/or pressure required for multiple detectors. Multiple pumps could also be utilized.

The present invention is particularly adapted for an off-line system since the hydrocarbon fluid containing the agent or additive is dissolved or micro-emulsified using the carrier.

As such, an invention has been disclosed in terms of preferred embodiments thereof which fulfill each and every one of the objects of the present invention as set forth above and provides a new and improved method and apparatus for determining and/or monitoring the presence/absence of agents/additives in hydrocarbon fluids, particularly motor oils.

Various changes, modifications and alterations from the teachings of the present invention may be contemplated by those skilled in the art without departing from the intended spirit of the scope thereof. Accordingly, it is intended that the present invention only be limited by the terms of the appended claims.

Example: Microemulsion Formula (O/W)

| | |
|---|---|
| Water | 38.5% |
| Arcosolv PM | 5.4% |
| Trycol 6964 | 5.6% |
| Tomah E-14-2 | 3.3% |
| Rhodacal 330 | 4.0% |
| Abex EP 110 | 2.1% |

-continued

| | |
|---|---|
| Isopar G | 38.5% |
| Igepal CA-210 | 2.7% |
| | 100.0% |

Example: Microemulsion Formula (W/O)

| Component | Composition |
|---|---|
| Mineral Spirits | 74.6% |
| Igepal CA-210 | 3.7% |
| Tomah E-14-2 | 4.5% |
| Trycol 6964 | 3.7% |
| Rhodafac RE-610 | 1.1% |
| Water | 12.3% |
| Total | 100.0% |

What is claimed is:

1. An apparatus for monitoring at least one electroactive antioxidant or antiwear agent in a hydrocarbon fluid comprising:
   a) a source of hydrocarbon fluid;
   b) a low pressure and low pulsation pump;
   c) a reservoir in communication with the pump for storing a carrier mobile phase capable of dissolving or emulsifying the hydrocarbon fluid;
   d) an injector located between the pump and the detector for injecting the hydrocarbon fluid into the carrier; and
   e) an electrochemical detector downstream of the injector which senses at least one of said agents in the hydrocarbon fluid.

2. The apparatus of claim 1 further comprising a back pressure regulator downstream of the electrochemical detector.

3. The apparatus of claim 1 wherein said pump operates in a pressure range of 5 to 500 psi.

4. The apparatus of claim 1 wherein the electrochemical detector is adapted to detect at least one of antioxidant and antiwear agents in the hydrocarbon fluid.

5. The apparatus of claim 1 wherein the pump operates with low pulsation whose effect on the background noise may not exceed one-third of the magnitude of the analytical signal from the electroactive antioxidant or antiwear agent (s) to be detected.

6. The apparatus of claim 1 further comprising a display for visual indicating a presence or absence of said at least one of said agents.

7. A method of monitoring for the presence of at least one electroactive antioxidant or antiwear agents in a hydrocarbon fluid comprising the steps of:
   a. providing a hydrocarbon fluid containing at least one electroactive antioxidant or antiwear agents;
   b. providing a carrier mobile phase capable of dissolving or micro-emulsifying the hydrocarbon fluid containing the said agents to be detected.
   c. injecting the hydrocarbon fluid into the mobile phase which then passes through an electrochemical detector; and
   d. sensing the mobile phase using the electrochemical detector to monitor for the presence or absence of said at least one agent and providing an indication of such presence or absence.

8. The method of claim 7 wherein the hydrocarbon fluid is an oil.

9. The method of claim 8 wherein the oil is engine oil or other lubricating oils containing at least one of electroactive antioxidant or antiwear agents.

10. The method of claim 7 wherein the at least one agent is an antioxidant such as hindered phenols or aromatic amines, or an antiwear agent, such as ZDDP.

11. The method of claim 7 wherein the carrier is pumped through the system with a low pressure pump operating at pressure between 5 and 500 psi.

12. The method of claim 7 wherein the carrier is a solvent.

13. The method of claim 12 wherein the solvent is selected from the group consisting of toluene, acetonitrile, ketones, alcohols, esters, amides, ethers, and room temperature liquid organic salts, which in general have a polarity in the molecule, an dielectric constant higher than 2.0, and an electrochemical window greater than 2 volts.

14. The method of claim 7 wherein the carrier is a microemulsion.

15. The method of claim 14 wherein the microemulsion consists of emulsifier(s), water, and oil.

16. The method of claim 15 wherein the emulsifiers are selected from the group consisting of non-ionic, anionic, cationic, and amphoteric surfactants.

17. The method of claim 7 wherein the mobile phase is discarded after said sensing.

18. The method of claim 7 wherein the hydrocarbon fluid is an engine oil and the at least one agent is one of electroactive antioxidant or antiwear agents.

19. The method of claim 7 wherein the sensing step is performed for a select period of time.

20. The method of claim 19 wherein said select period of time is less than 5 minutes.

* * * * *